United States Patent [19]

Gjerlov

[11] Patent Number: 5,038,396
[45] Date of Patent: Aug. 6, 1991

[54] PREPARATION FOR REHYDRATING MONOGASTRIC ANIMALS, INCLUDING NEW-BORN CALVES, PIGS AND HUMAN BEINGS SUFFERING FROM DIARRHOEA AND USE THEREOF

[76] Inventor: Mogens Gjerlov, DK-5672 Broby, Nr. Broby, Denmark

[21] Appl. No.: 378,591

[22] Filed: Jul. 11, 1989

Related U.S. Application Data

[63] Continuation-in-part of Ser. No. 76,126, Jul. 21, 1987, abandoned, which is a continuation-in-part of Ser. No. 740,840, May 28, 1985, abandoned.

[51] Int. Cl.$^5$ .................. A61K 35/78; A61K 33/42; A61K 33/80
[52] U.S. Cl. .................. 424/195.1; 424/601; 424/611; 424/682; 514/53; 514/867
[58] Field of Search .................. 424/94.61, 195.1, 611, 424/682, 601; 564/53, 867

[56] References Cited

U.S. PATENT DOCUMENTS

| | | | |
|---|---|---|---|
| 3,449,492 | 6/1969 | Jensen | 424/682 |
| 3,898,328 | 8/1975 | Beigler | 424/681 |
| 4,009,268 | 2/1977 | Cardon | 514/60 |
| 4,010,262 | 3/1977 | Cardon | 514/60 |
| 4,083,960 | 4/1978 | Yamashita | 424/94.61 |
| 4,164,568 | 8/1979 | Bywater | 424/677 |

FOREIGN PATENT DOCUMENTS

| | | |
|---|---|---|
| 8202650 | 8/1982 | Denmark . |
| 2455281 | 6/1975 | Fed. Rep. of Germany . |
| 2626109 | 12/1976 | Fed. Rep. of Germany . |
| 2644197 | 5/1977 | Fed. Rep. of Germany . |
| 2611979 | 9/1977 | Fed. Rep. of Germany . |
| 940555 | 12/1964 | France . |
| 1306752 | 2/1971 | United Kingdom . |
| 1569866 | 5/1978 | United Kingdom . |

OTHER PUBLICATIONS

Niyuugivou, Meiju and Kokuby, Shigeji, "Composition for Remedying Diarrhoea of Domestic Animals", Abstract of JP Application No. 58-39625.
Websters Dictionary definition of "Corrigent".
Websters Dictionary definition of "Intumescent".
"Ispaghula Husk", *British Pharmacopeia*, 1980.
White, D. G., Moss, P., Groutides C., Verschoor, J., "An Experimental Model of Calf Diarrhoea and Evaluation of Treatment with an Oral Electrolyte Preparation", Deptment of Medicine Royal Veterinary College.
"Diabetes Today", Report on the British Diabetic Assoc. Meeting on Dietary Fibre in the Management of the Diabetic, 1984.
"New Rehyrdation Method, Using Mucopolysacchrides from Isphagula Husk in Combination with Glucose and Electrolytes", Pharmalett International B.V.

*Primary Examiner*—John W. Rollins
*Attorney, Agent, or Firm*—Merchant, Gould, Smith, Edell, Welter & Schmidt

[57] ABSTRACT

A preparation for rehydrating monogastric animals including human beings and new-born ruminants suffering from diarrhoea which preparation is intended for being mixed in water comprises an absorbent intumescent agent, electrolytes, glucose and lactose-decomposing enzyme(s)—being present in the form of lactose-decomposing enzyme(s) added as such or present as a part of at least one of the other components—i.e. component(s) not being lactose-decomposing enzyme(s) added as such—and possibly filler(s), taste corrigent(s) and coloring agent(s).

15 Claims, 2 Drawing Sheets

FIG. 1A
Villous cells
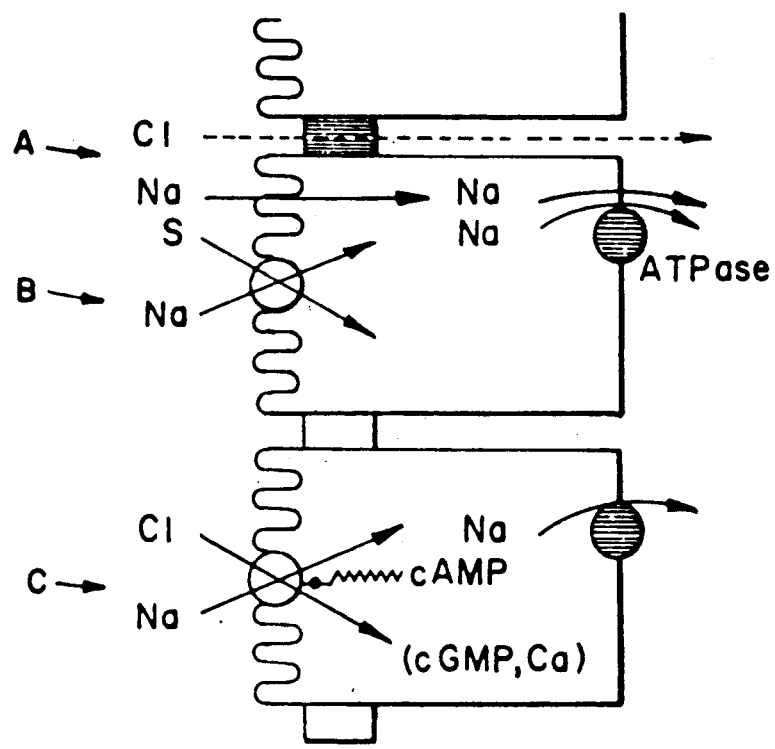
FIG. 1B
Crypt cells
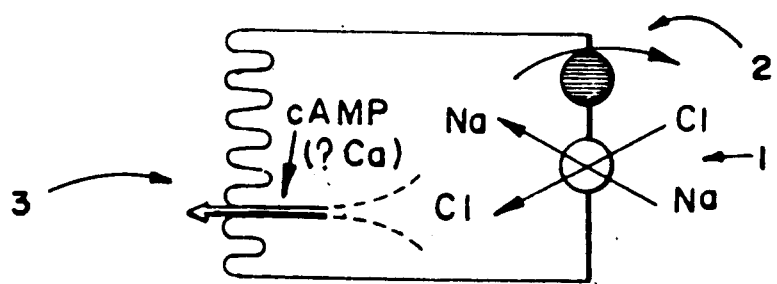
FIG. 1

PREPARATION FOR REHYDRATING MONOGASTRIC ANIMALS, INCLUDING NEW-BORN CALVES, PIGS AND HUMAN BEINGS SUFFERING FROM DIARRHOEA AND USE THEREOF

CROSS REFERENCE TO RELATED APPLICATIONS

The present application is a continuation-in-part application of U.S. Ser. No. 076,126 filed Jul. 21, 1987, which is a continuation-in-part application of U.S. Ser. No. 740,840 filed May 28, 1985, now abandoned.

FIELD OF THE INVENTION

The invention relates to a preparation for rehydrating monogastric animals, including human beings, suffering from diarrhoea, especially non-infectious diarrhoea and diarrhoea caused by rota and corona viruses.

BACKGROUND

Even in well-organized agricultural countries with good veterinary coverage, the mortality among new-born animals such as calves and pigs is still very high. For example, in Denmark in 1980 there were destroyed about 180,000 calves, which corresponds to nearly 20% of the calves born every year. The cause of a number of the deaths among calves, and also of a number of corresponding deaths among sucking pigs, is that they become stressed when they are weaned and placed for example, in common sties or folds. When the animals are removed and thus no longer receive mother's milk, right up to half of the animals develop diarrhoea because they become stressed due to change of fodder, transportation etc. It is assumed that half of the deaths are due to diarrhoea which arises within the first month after their birth. A number of the calves also suffer from rota and corona virus infection, which is a contagious intestinal infection where cows are virus carriers and infect the calves. The disease is caused by i.a. strongly reduced production of lactase, so that the animals cannot decompose the lactose in the milk with which they are fed, and hereafter diarrhoea is quickly developed by osmotic effect in the intestinal canal. New-born calves and pigs with diarrhoea will loose considerably in weight because of dehydration and many die.

The object of the invention is to present a preparation for the treatment of diarrhoea, so that a very large number of the sick animals can be cured in very few days, whereby deaths due to loss of fluid is avoided and for the calves a higher growth rate is obtained.

SUMMARY OF THE INVENTION

A preparation for rehydrating monogastric animal s including human beings and new-born ruminants suffering from diarrhoea, which preparation is intended for being mixed in water, comprises an absorbent intumescent agent, electrolytes and lactose-decomposing enzyme(s)—being present in the form of lactose-decomposing enzyme(s) added as such or present as a part of at least one of the other components —i.e. component(s) not being lactose-decomposing enzyme(s) added as such—and possibly filler(s), taste corrigent(s) and coloring agent(s). The intumescent agent constitutes 20-70% according to weight, preferably 40-43%, the electrolytes constitute 40-60% according to weight, preferably 53-57%, and—if present as a result of being added as such—the enzyme constitutes or enzymes constitute 0.01-5% according to weight, preferably 0.025-0.027% and the balance is made up of filler(s), taste corrigent(s) and/or coloring agent(s).

In this connection it is noted that it was found—when investigated—that not only does a preparation comprising a lactose-decomposing enzyme show the ability to decompose lactose but also the water binding swelling agent Isphagula Husk as such shows a considerable ability to decompose lactose which is even more true of a preparation comprising no lactose-decomposing enzyme(s) added as such but comprising a water binding swelling agent consisting of Isphagula Husk as the ability of this last mentioned preparation to decompose lactose is only somewhat less than the ability of that first mentioned preparation to decompose lactose (A description of the investigation and the results thereof are given hereinbelow.).

It has been proven particularly advantageous that the intumescent agent is vegetable fibres from the family plantaginacea and—if present as a result of being added as such—the enzyme is lactase with pH-optimum between 2 and 10 and the electrolytes are a mixture of two or more of the substances magnesium oxide, citric acid, potassium chloride sodium citrate, sodium chloride, sodium bicarbonate and glucose. An optimum effect is achieved when the fibres are dried crushed seed coats of plantago ovata.

An agent for rehydrating animals suffering from diarrhoea which may be cured in very few days is thereby obtained, thus avoiding deaths and loss of weight. The vast majority of cases of non-infectious diarrhoea among one-stomached animals can be cured in a very few days.

DETAILED DESCRIPTION OF THE INVENTION

The object of the present invention is achieved by composing the preparation having an absorbent intumescent, electrolytes, lactose-decomposing enzyme(s) —being present in the form of lactose-decomposing enzyme(s) added as such or present as a part of at least one of the other components—i.e. component(s) not being lactose-decomposing enzyme(s) added as such— —and perhaps filler(s), tase corrigent(s) and/or coloring agent(s). Surprisingly, it has been shown that a mixture of an absorbent intumescent agent or water binding swelling agent, lactose-decomposing enzyme(s)—being present in the form of lactose-decomposing enzyme(s) added as such or present as a part of at least one of the other components —i.e. component(s) not being lactose-decomposing enzyme(s) added as such—and one or more electrolytes is a quick and effective agent against diarrhoea without any apparent side effects and with a better effect than with the individual components alone. The agent can be used for treatment of diarrhoea among all offspring of ruminants as long as these are one-stomached, i.e. before they have begun cud-chewing, and for the treatment of non-infectious diarrhoea and diarrhoea caused by rota and corona viruses among all other one-stomached animals, including human beings. The lactose-decomposing enzyme—being present in the form of lactose-decomposing enzyme(s) added as such or present as a part of at least one of the other components—i.e. component(s) not being lactose-decomposing enzyme(s) added as such —decompose that lactose which. for example, a calf suffering from diarrhoea is itself unable to decompose and digest. Nondecomposed lactose in the intestinal canal contributes to worsening an attack of diarrhoea. With certain other methods of treatment, it has been suggested that the lactose be decomposed in the milk before the calf receives the milk, but with the preparation according to the invention, the lactose is not decomposed until inside the calf's stomach and intestine which results in fewer side effects, for example in the form of sitiophobia.

The agent is produced quite simply by weighing out and mixing the individual parts so that the finished agent is supplied as a dry powder ready for use.

Another great advantage of the preparation according to the invention is that it is possible to cure animals of diarrhoea without the use of normal antibiotics, and thus avoiding the disadvantages herewith in the form of medicinal residues in the animal, and possibilities of developing bacteria strains resistant to antibiotics.

According to the invention it is very advantageous that the electrolytes in the preparation comprise such salts that replace salt lost by diarrhoea since by rehydration it is merely necessary to administer a preparation which will bring about both rehydration or stop dehydration and provide the lost salts and fluid. The electrolytes are composed in such a manner that they give a buffer effect in the preparation in solution or suspension.

When as disclosed the preparation comprises a buffer, it is not necessary to protect the enzyme(s) by adopting special measures since the preparation itself for a period of up to 6 hours stabilises the pH-value of the stomach so that the enzyme(s) are not inactivated, and it is not necessary to wait for the dissolution of a coating or the like in the intestine, the enzyme(s) being immediately ready to perform its/their function—this/these enzyme(s) being present in the preparation of the invention in the form of lactose-decomposing enzyme(s) added as such or being present in the preparation of the invention as a part of at least one of the other components—i.e. component(s) not being lactose-decomposing enzymes added as such. Thus the protective measures for the enzyme(s) are also saved.

The component parts must be such which are pharmaceutically tolerable and a combination of the parts makes it possible to achieve the object of the present invention.

The intumescent is selected from among vegetable fibres from the family plantaginacea, seeds or vegetable matter from the family linum, pectin, hemicellulose, carboxymethyl cellulose, methyl cellulose, perhaps pregelatinised starch and albomine tannate. The electrolytes are a mixture of two or more of the substances magnesium oxide, magnesium carbonate hydroxide, magnesium hydroxide, magnesium silicate, calcium silicate, calcium carbonate, alkali metal chlorides such as sodium or potassium chloride, alkali metal hydrogen carbonates such as sodium or potassium hydrogen carbonate, aluminum phosphate, aluminum hydroxide, citric acid and alkali metal citrates such as sodium or potassium citrate. The enzyme(s)—if present as a result of being added as such—is/are a lactase or lactases with pH-optimum between 2 and 10, the filler is a fibre material such as bran, especially wheat bran, and the coloring agent is a pharmaceutically tolerable coloring agent.

By composing the preparation wherein the electrolytes are a mixture of magnesium oxide, sodium chloride, potassium chloride, sodium hydrogen carbonate, citric acid, sodium citrate and glucose; the enzyme —if present as a result of being added as such—is lactase with a pH-optimum between 5 and 8; the filler is wheat bran; and, the coloring agent is terra rubrum; there is obtained a simple preparation which has the properties required, i.e. stopping diarrhoea, providing the necessary salts, providing lactase(s) and bringing it uninfluenced through the stomach in a simple manner.

It is especially advantageous to compose the agent with vegetable fibres from the family plantaginacea as an intumescent the reason being that it has been known that the absorbent vegetable fibres swell up in the intestine in a very suitable and natural manner, which gives the contents of the intestine a gelatinous consistency so that the faeces will have a normal consistency already a few hours after the first feeding with the agent. The more quickly that a diarrhoea from which a calf or sucking pig is suffering is brought under control, the greater are the chances of the animal surviving. The glucose content and the necessary salts in the correct amounts will promote the absorption of nutrients and give the weakened animal an easily transformable energy.

Practical applications and experiments have shown that the agent according to the invention is particularly effective when the fibres are seed coats comprising bran or a filler. Specifically, the fibres are in the form of dried, crushed seed coats of Plantago ovata.

The relation between the individual components in the preparation according to the invention can vary greatly, but it has been shown that the optimum effect and protection of the enzymes is achieved if the individual components are used in the following amounts: the intumescent constitutes 20-70% by weight; the electrolytes constitute 40-60% by weight; the enzyme or enzymes—if being present as a result of being added as such—constitute 0.01-5% by weight; and the balance is made up of filler(s) and perhaps taste corrigent(s) and/or coloring agent(s). If this agent is used immediately when an animal shows the symptoms of diarrhoea, and it is a question of so-called problem stock, then the agent according to the invention should be used in the event of the animal merely refusing to drink up, and a case of diarrhoea can normally be stopped merely by treating the animal a few times. It is thus possible to put an immediate stop to the life-threatening loss of water and salts (electrolytes) so that by far the majority of the animals attacked will survive and be restored to health quicker than if they are only treated with electrolytes alone or the water palliative fibres alone. This quicker restoration of the animals will therefore bring about a better growth which has been proved by clinical experiments.

A preparation characterized in that as an intumescent it contains 40% by weight Isphagula Husk, 52.925% by weight electrolytes which are made up of 0.575% by weight magnesium oxide, 1.35% by weight citric acid, 2.4% by weight potassium chloride, 2.65% by weight sodium citrate, 4.15% by weight sodium chloride, 6.8% by weight sodium hydrogen carbonate and 35% by weight glucose calculated on the finished preparation, 0.025% by weight lactase, 6.8% by weight filler in the form of wheat bran and 0.25% by weight coloring agent in the form of terra rubrum, will stop diarrhoea among animals and provide rehydration since the preparation will only have to be mixed in water or milk or a water/milk mixture whereupon an animal will willingly drink it.

For human application the preparation is composed without filler and coloring agents but with a taste corrigent. Preferably the composition is characterized in that as the intumescent it contains approximately 43% by weight Isphagula Husk being ground, approximately 57% by weight electrolytes which are made up of 0.17% by weight magnesium oxide, 1.45% by weight citric acid, 2.575% by weight potassium chloride, 2.845% by weight sodium citrate, 4.456% by weight sodium chloride, 7.3% by weight sodium bicarbonate, 37.58% by weight glucose calculated on the finished preparation, 0.027% by weight lactase and 0.2% by weight taste corrigent in the form of oil of peppermint. This composition is particularly preferred since such a preparation is effective and at the same time has a pleasant taste.

Since vegetable fibres as disclosed herein are expensive to use, it is possible to replace the organic absorbent intumescent with a synthetic intumescent in the form of carboxymethyl cellulose in different configurations with various radicals and various metals can be used. Innumerable different carboxymethyl celluloses are known and all of these can be used, but with different effect, the reason being that they are available with both different viscosity and different rates of intumescence. The use of a synthetic intumescent results in cheaper product, and generally with sufficient applicability.

The preparation according to the invention is used by pouring 40–55 g of the mixture into preferably 1:1 of lukewarm water, milk or a water/milk mixture at around 38° C. The preparation is then administered orally. The result is a mixture which the animals are very willing to drink and which quickly cures them of diarrhoea because the gel formed by the agent in the intestinal canal has the following characteristics:
  a) a protective effect on the actual intestinal mucosa,
  b) binds some of the bacteria and their toxins to itself,
  c) ensures a normal intestinal passage (peristalsis),
  d) quickly stops the loss of fluid and electrolytes,
  e) buffers the capacity due to the added electrolytes in the gel formed, protects the added lactase from inactivation for up to 6 hours. and
  f) the lactase—being present in the form of lactose-decomposing enzyme(s) added as such or present as a part of at least one of the other components—i.e. component(s) not being lactose-decomposing enzyme(s) added as such—decomposes the lactose in the intestine and thus recreates a normal osmotic balance.

For human application the same results as mentioned above will be obtained. If desired, cold liquid can be used for the preparation.

BRIEF DESCRIPTION OF THE DRAWINGS

FIG. 1 is a schematic representation of sodium absorption and chlorine secretion.

DETAILED DESCRIPTION OF THE INVENTION

Figure 2:
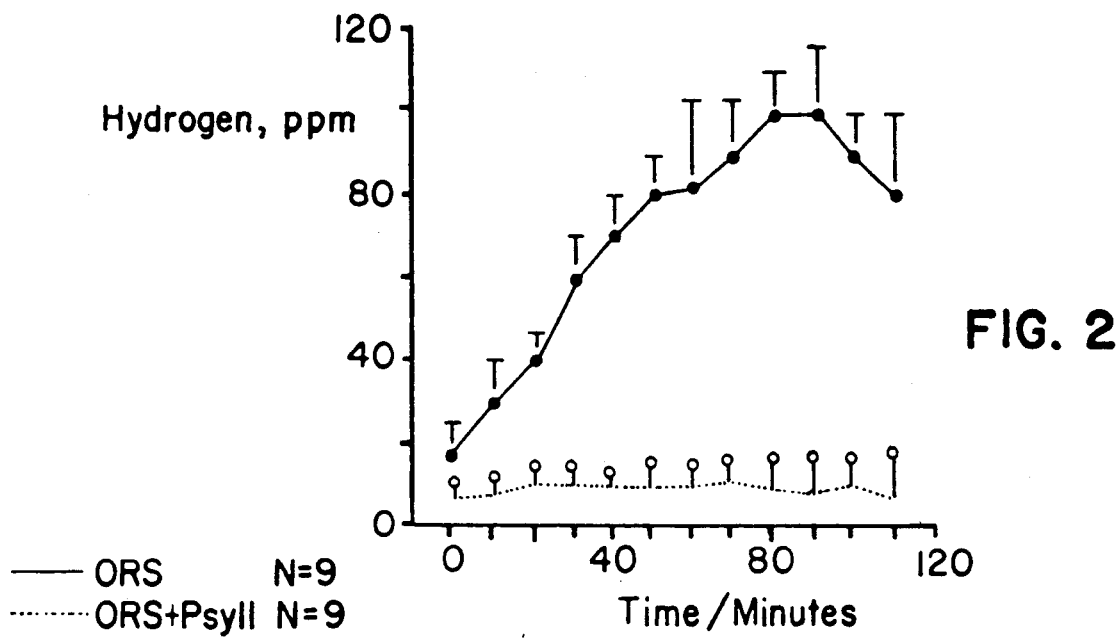
FIG. 2 is a graph representing average hydrogen response in patients treated with ORS, or ORS plus Psyll.

Referring to the drawings for detail:

FIG. 1 relates to the mechanism of sodium absorption, and the mechanism of chlorine secretion. At reference A is shown uncoupled, electrogenic sodium diffusion, accompanied by passive chlorine absorption. At reference B is shown sodium absorption coupled to absorption of organic solute(s) such as sugars and neutral amino acids. At reference C is shown neutral NaCl transport, which is inhibited by elevated levels of c. AMP and probably also C. GMP and Ca.

Referring to chlorine secretion:

At reference 1, neutral sodium chloride co-transport into the cell is indicated. At reference numeral 2, extrusion of sodium is indicated. At reference numeral 3, c. AMP stimulated mucosal permeability (conductance) increase for chlorine, is represented.

Referring to FIG. 2:

FIG. 2 indicates the average responses obtained for two hours following the first observed increase in breath hydrogen. In the patients treated with ORS absorbed to PO muciloid, the mean $H_2$ response was 18 ppm/2 hours $\pm 28.7$ SD. In the group treated with ORS only, the $H_2$ response amounted to 85 ppm/2 hours $\pm 58.8$ SD.

Figure 3:
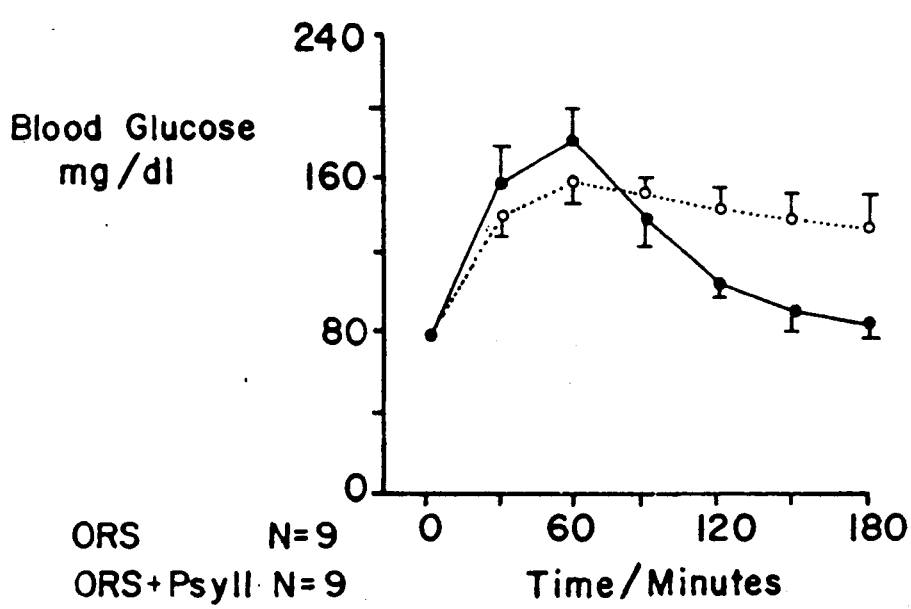
FIG. 3 is a graph indicating blood glucose concentrations in patients treated with ORS only, and with ORS absorbed to PO mucill.

Referring to FIG. 3:

Mean$\pm$SD blood glucose concentrations in patients treated with ORS only, and with ORS absorbed on PO mucill are represented. The area under the glucose concentration time curve for ORS (9,437 mgr/dl/min.$\pm$3,475 SD) was significantly lower than for ORS with PO musyloid (15,013 mgr/dl/min. $\pm$4,135 SD).

It is a well known fact that the absorption of fluid from the intestine during rehydration is mostly determined by the absorption of sodium. Of the three different mechanisms for sodium uptake, solute (e.g. glucose) dependant for sodium absorption is particularly important from a therapeutic point of view since this process is usually unaffected by infectous processes.

The use of glucose electrolyte mixtures (G.E.M.) is based upon this therapeutic concept (see FIG. 1). However, our research has shown that part of the glucose of the classic G.E.M. compositions as advised by the WHO is not absorbed and cannot as a consequence contribute to the above rehydration.

This glucose malabsorption was indicated by the breath hydrogen test (B.H.T.). This test is based on the observation that hydrogen is produced in the colon when carbohydrates are fermented by colonic bacteria; this hydrogen is excreted by the lungs.

The hydrogen response in patients treated with a standard G.E.M. containing per liter $Na^+$ 90 mmol, $K^+$ 20 mmol, $Cl^-$ 80 mmol, HCO 30 mmol and glucose 111 mmol amounted to 85 ppm/2 hrs$\pm$5B.B SD, N=9 indicating a considerable malabsorption of glucose (see FIG. 2 in which ORS is used instead of G.E.M., and PO mucolloid and Psyll respectively instead of lsphagula).

The use of lsphagula in the form of lsphagula Husk in combination with glucose and electrolytes was previously, rather initially chosen for the protective properties mucopolysaccharides could offer in the gut.

Ispahgula differs from other gel forming polysaccharides because:
  1. The polyxylose backbone is not broken down either by intestinal enzymes or by the intestinal flora with one exception, viz. bacteroides ovates.
  2. Isphagula contains a high amount (proportion) of galactose and residues mimicing the structure of the membrane receptors on the enterocytes and offers in this way an aspecific binding capacity for various pathogenic micro-organisms.

A disadvantage of adding the Isphagula was the expected influence on the glucose absorption because it was known the Isphagula—like other gel forming fibers—descreased the glucose in healthy subjects, see "Diabetes Today" reporting on the British Diabetes Association meeting Dietary Fibre in the Management of the Diabetic held at the Royal College of Physicians, June 1984.

In order to limit this effect on the glucose absorption as much as possible the Isphagula was not mixed into the feed but brought into suspension in a fluid together with, i.e. also containing the glucose and electrolytes in order to saturate the mucopolysaccharides with glucose to and prevent further absorption to the Isphagula within the intestine. This measure forms the basis of the indication in the specification as originally filed, page 12, lines 5-8 and the statement in the originally filed claim 12, especially the three last words.

Quite unexpectedly, however, or much to our surprise the total glucose absorption in enteritis patients treated with the same G.E.M. absorbed to the Isphagula (20 grams per liter) exceeded the glucose absorption treated with the G.E.M. only.

The area under the glucose concentration vs. time curve (see FIG. 3 in which ORS is used instead of G.E.M. and PO mucill(oid) and Psyll respectively instead of Isphagula) for the G.E.M. (9.347 mg/dl/min ±3.475 SD) was significantly lower than for the G.E.M. with Isphagula (15.013 mg/dl/min ±4 135 SD) and the hydrogen production in the G.E.M./Ispahgula group amounted to 18 ppm/2 hrs ±28.7 SD only (see the above mentioned FIG. 2).

Breath hydrogen response is considered low internationally when the mean concentration is less than 20 ppm.

Not wishing to be bound by any theory we are of the opinion that this unexpected—or surprising—finding can be explained by the fact that in healthy subjects the mucous layer plays a role in the transport of food ingredients through the intestinal wall.

In most intestinal infections the mucous layer is broken down. Preliminary results from electron microscope pictures and phase contrast microscopy indicate that the mucous produced by the Isphagula replaces the damaged mucous layer in the subjects suffering from intestinal infections in such a way that it acts as a bioadhesive polymer which can—although we do not wish to be bound by any theory—explain the enchanced glucose absorption.

The big advantage of this increased glucose absorption is that as consequence more sodium and water is absorbed thus stimulating rehydration.

It cannot be stressed strongly enough that this increased glucose absorption can only be achieved by saturating the Isphagula with glucose before intake and is only present in subjects suffering from intestinal infections.

Under other circumstances, e.g. if the Isphagula is mixed into the feed or is not brought into suspension in a fluid together with, i.e. also containing glucose, the intake will lead to a decrease in glucose absorption and thus worsen the rehydration situation of the subject in question.

The above measures and/or actions lead to reasoned unexpected or surprising findings, moreover, using Isphagula counters to the above expected disadvantage in a rehydration situation in the form of a decreased glucose absorption—albeit in healthy subjects.

Investigation of the ability of some materials to decompose lactose

In order to compare the lactase activity of a preparation comprising a lactose-decomposing enzyme with the lactase activity of Isphagula Husk as such and a preparation comprising no lactose-decomposing enzyme but comprising a water binding swelling agent consisting of Isphagula Husk the mixtures 1, 2 and 3 given below were prepared.

Mixture 1

Isphagula Husk 16.8 grams
Lactase CHBS 25000 0.011 grams
Tap water 1 liter

Mixture 2

Isphagula Husk 16.8 grams
Tap water 1 liter

Mixture 3

Isphagula Husk 16.8 grams
Sodium bicarbonate 3.05 grams
Sodium citrate 1.18 grams
Potassium chloride 1.07 grams
Citric acid 0.60 grams
Magnesium hydroxide 0.33 grams
Tap water 1 liter The components of the mixtures 1, 2 and 3 were mixed for 5 minutes.

A sample of 50 milliliters was taken from all three suspensions. The samples were centrifuged for one hour at 14.000 g.

The supernatants were removed for the determination of lactase activity.

The results of the determination of lactase activity are given in table 1. In table 1 the relative lactase activity of mixtures 2 and 3 is given, the lactase activity of mixture 1 being rendered as 100%.

TABLE 1

| Mixture No. | (Relative) lactase activity |
| --- | --- |
| 1 | 100% |
| 2 | 39% |
| 3 | 91% |

From table 1 it is found that mixture 3 shows a relative lactase activity of 91% which means that it is possible to omit the addition of lactase as such. From table 1 it is obvious that the components besides Isphagula Husk present in mixture 3 produce a strong enhancement of the lactase activity stemming from the Isphagula Husk.

It is also noted that it has been found that there exists a mutual or two-way correspondence between on the one hand the group of abilities to decompose lactose consisting of the ability of the preparation comprising lactose-decomposing enzyme added as such to decompose lactose as given in table 1 and the ability of the preparation comprising no lactosedecomposing enzyme(s) added as such to decompose lactose as given in table 1 and on the other hand the group of efficiencies—found in actual use—of the preparation of the invention in the treatment of diarrhoea —in other words effciencies—found in actual use—in achieving the object of the invention, in particular the cardinal point of the object of the invention, viz. the treatment of diarrhoea—consisting of the efficiency—found in actual use—of the preparation of the invention comprising lactose-decomposing enzyme(s) added as such in the treatment of diarrhoea and the efficiency—found in actual use—of the preparation of the invention comprising no lactose-decomposing enzyme(s) added as such in the treatment of diarrhoea.

Practical experiment with the preparation according to the invention 480 sucking calves, all of them two or three weeks old, were taken in for rearing experiments under uniform optimum conditions with regard to hygiene, climate and feeding, the object being to test the effect of the preparation on dietetic-conditioned diarrhoea among sucking calves.

By the first feeding after the calves taken in had been placed in the cow-house at the research station, all of the calves each received three liters of a conventional electrolyte/water mixture, after which this was gradually changed during the course of five days to up to 7 liters of milk substitute. The calves also had free access to hay and ordinary fodder supplements.

During the course of fourteen days from the time they were taken in, 86 of the calves, i.e. 17.9%, contracted stomach/intestinal disturbances. These animals were immediately treated with the preparation according to the invention and as disclosed in claim 9.

73 of the sick calves, i.e. 84.9% were completely cured within a few days. The 13 calves which were not cured immediately by the treatment were then given supplementary treatment with antibiotics.

From this it will be seen that the diarrhoea which is contracted early by many calves fattened on full milk and by sucking pigs is often due to virus infections and to transport stress, stress as a result of feeding change and stress from changed environment etc., and can therefore be cured with the preparation according to the invention without the use of antibiotics. Only 13 animals out of 86, i.e. approx. 15%, required supplementary antibiotic treatment.

Course of treatment when using the preparation

The agent is mixed in water and is dosed in accordance with the weight of the animal, the amounts used being as stated in the following table, viz. table 2:

TABLE 2

| Weight of animal | Dose per feeding | No. of feeds per 24 hours |
| --- | --- | --- |
| approx. 20 kg | ½ l water + approx. 25 g | 4 |
| approx. 30 kg | 1 l water + approx. 50 g | 4 |
| approx. 40 kg | 1½ l water + approx. 75 g | 3–4 |
| approx. 50 kg | 2 l water + approx. 100 g | 3 |
| approx. 60 kg | 2½ l water + approx. 125 g | 3 |

After the first twenty-four hours, it can be an advantage to add 25–50 g curdled milk product, for example scoured milk, yoghurt, junket or the like, per liter. From the third day, one can gradually change over to the normal mixed fodder.

There are also cattle stock among which stomach/intestine disturbances are a recurrent problem. In such cases it can be an advantage to give for example the calves the preparation according to the invention as soon as they just refuse to drink up the normal feed, for example consisting of full-cream milk or other milk mixtures or the like.

Comparative Experiment

The curative properties against diarrhoea of the preparation according to the invention were compared by a controlled experiment with the properties of Calmix neo at a Dutch calf fattening station.

For the experiments there were used in all 230 calves which were divided in 5 groups of 46 animals each. They were placed in wooden pens with floor grating and being ventilated. One week old calves were used. The animals were weighed before the experiment, after 29 days and after 58 days. At the beginning there is given 1.5 l water and 75 g electrolytes as first feeding. The fodder consisted of a bag of Heftica per calf followed by Hemeka start and fattening according to the usual schedule.

In case of diarrhoea either the preparation according to the invention or Calmix neo is given.

The experiment results are given in the table below, viz. table 3:

TABLE 3

| Average results Curative treatment No. of calves | Conservative treatment (Calmix neo) 15 | Preparation according to the invention 15 |
| --- | --- | --- |
| Average weight | | |
| at start | 41.6 kg | 38.3 kg |
| after 29 days | 47.5 kg | 45.3 kg |
| after 58 days | 74.4 kg | 73.7 kg |
| Average weight | | |
| after 29 days | 5.9 kg | 7.0 kg |
| after 58 days | 32.8 kg | 35.4 kg |
| Average weight | | |
| after 29 days | 5.9 kg | 7.0 kg |
| after 58 days | 26.9 kg | 28.4 kg |
| Average weight/day | | |
| after 29 days | 203 g | 241 g |
| after 58 days | 565 g | 610 g |

The curative properties of the preparation prove to be good. After 58 days the calves showed an average of 2.6 kg larger growth than the control group which was treated with Calmix neo. Moreover, the average weight per day among the animals which were treated with the preparation according to the invention, increased in the second period more than the animals treated with Calmix neo. This shows that not only are the absorption and the digestive capacity of the intestine less influenced but they are at the same time more quickly recreated. This result supports the fact that the pharmocokinetics of the preparation according to the invention builds on a protection of the intestinal wall against pathogenic attacks coupled with a compensation for lack of lactose by means of acid resistant lactase whereby the secretion as well as the osmotic component are combatted.

EXAMPLE 1

The preparation according to the invention can be composed, for example, as follows:

| 1000 g contains: | | |
| --- | --- | --- |
| Magnesium oxide | 5.75 g | electrolytes |
| Citric acid | 13.50 g | electrolytes |
| Potassium chloride | 24.00 g | electrolytes |
| Sodium citrate | 26.50 g | electrolytes |
| Sodium chloride | 41.50 g | electrolytes |
| Sodium bicarbonate | 68.00 g | electrolytes |
| Glucose | 350.00 g | electrolytes |

-continued

| 1000 g contains: | | |
|---|---|---|
| Terra rubrum | 2.50 g | coloring agent |
| Wheat bran | 68.00 g | filler |
| Isphagula Husk (dried seed coats of plantago ovata) | 400.00 g | absorbent fibre |
| Lactase | 0.25 g | enzyme |
| | 1000.00 g | |

The individual ingredients, all of which are available as dry powders, are mixed mechanically and are thereafter immediately ready for use.

The agent according to the invention must not be administered in dry form, but must be suspended in water and administered as a solution or suspension. The intumescence occurs hereafter in the intestinal canal during a suitable period, whereby by absorption of fluid said intumescent swells up and gives the contents of the intestine a suitable consistency, and binds and receives some of the bacteria and their toxins so that a diarrhoea is at once stopped.

EXAMPLE 2

The preparation according to the invention can also have the following composition which is particularly preferred for human application:

| 1000 g contains: | |
|---|---|
| Magnesium oxide | 6.17 g |
| Citric acid | 14.50 g |
| Potassium chloride | 25.75 g |
| Sodium citrate | 28.45 g |
| Sodium chloride | 44.56 g |
| Sodium bicarbonate | 73.00 g |
| Glucose | 375.80 g |
| Isphagula Husk, crushed | 429.50 g |
| Lactase | 0.27 g |
| Oil of peppermint | 2.00 g |

EXAMPLE 3

A suspension or solution of the preparation prepared in example 1 is produced by mixing 50 g preparation to 1 liter of water. The pH-value in the fresh preparation is 8.56. By titration to a pH-value of 5.73 there is used 40.5 meq hydrochloric acid which shows that there is a not inconsiderable buffer effect in the preparation which will "neutralise" the hydrochloric acid in the stomach and consequently protect the lactase.

The chemicals used in the examples are ordinary commercial chemicals and the lactase is preferably CHBS lactase 25000 from Chr. Hansens Laboratorium, Copenhagen.

What is claimed is:

1. A preparation for rehydrating monogastric animals, including human beings, suffering from diarrhoea, said preparation comprising:
   a) 20–70% by weight of a water binding swelling agent consisting essentially of Isphagula Husk; and
   b) 40–60% by weight electrolyte and glucose.

2. The preparation of claim 1, further comprising at least one filler, at least one taste corrigent and at least one coloring agent.

3. The preparation of claim 1 wherein said electrolyte comprises at least one salt which is a salt lost by diarrhoea.

4. The preparation of claim 1 wherein said electrolyte is composed to give a buffer effect in the preparation in solution or suspension.

5. The preparation of claim 1 wherein the electrolyte is a mixture of at least two of the substances selected from the group consisting of magnesium oxide, magnesium carbonate hydroxide, magnesium hydroxide, magnesium silicate, calcium silicate, calcium carbonate, sodium chloride, potassium chloride, sodium hydrogen carbonate, potassium hydrogen carbonate, aluminum phosphate, aluminum hydroxide, citric acid, sodium citrate, potassium citrate.

6. The preparation of claim 1 wherein the electrolyte is a mixture of at lest two of the substances selected from the group consisting of magnesium hydroxide, sodium chloride, potassium chloride, sodium hydrogen carbonate, citric acid and sodium citrate.

7. The preparation of claim 1 wherein the preparation further includes a filler.

8. The preparation of claim 7 wherein the filler is a fibrous bran material.

9. The preparation of claim 7 wherein the fiberous bran material is wheat bran.

10. The preparation of claim 1 wherein the preparation further includes a pharmaceutically acceptable coloring agent.

11. The preparation of claim 10 wherein the coloring agent is terra rubrum.

12. A preparation for rehydrating monogastric animals, including human beings, suffering from diarrhoea comprising: 20–70% by weight of Isphagula Husk as a swelling agent: 40–60% by weight including electrolyte and glucose; and the balance including at least one filler, said percents by weight calculated with respect to the amount of the swelling agent, electrolyte, and glucose and the balance taken collectively, and that the amount of the individual components chosen in a way so that the total of the percents by weight is 100.00.

13. The preparation according to claim 12 wherein said balance further includes at least one coloring agent.

14. The preparation according to claim 12 wherein the balance of said preparation further includes at least one taste corrigent.

15. Preparation for rehydrating monogastric animals, including human being suffering from diarrhoea comprising: 20–70% by weight of Isphagula Husk as a swelling agent; 40–60% by weight of electrolyte and glucose; and the balance including at lest one taste corrigent, where the percents by weight are calculated with respect to the amount of the swelling agent, electrolyte and glucose and the balance taken collectively, and that the amount of the individual components are chosen in such a way that a total of the percent by weight is 100.00.

* * * * *